(12) United States Patent
Cueto Garcia

(10) Patent No.: US 9,808,484 B2
(45) Date of Patent: Nov. 7, 2017

(54) ANTI-INFLAMMATORY COMPOSITION FOR AIDING AND PROMOTING THE HEALING OF CHRONIC ULCERATIVE LESIONS

(71) Applicant: Pebisut De Mexico S.A. DE C.V., Col. Lmas de Virreyes, C.P. (MX)

(72) Inventor: Jorge Cueto Garcia, Col. Bosques de las Lomas C.P. (MX)

(73) Assignee: Pebisut De Mexico S.A. DE C.V., Col. Lmas de Virreyes (MX)

( * ) Notice: Subject to any disclaimer, the term of this patent is extended or adjusted under 35 U.S.C. 154(b) by 68 days.

(21) Appl. No.: 15/026,280

(22) PCT Filed: Oct. 1, 2014

(86) PCT No.: PCT/MX2014/000152
§ 371 (c)(1),
(2) Date: Mar. 31, 2016

(87) PCT Pub. No.: WO2015/050425
PCT Pub. Date: Apr. 9, 2015

(65) Prior Publication Data
US 2016/0243162 A1  Aug. 25, 2016

(30) Foreign Application Priority Data
Oct. 2, 2013 (MX) .................. MX/a/2013/011471

(51) Int. Cl.
| | | |
|---|---|---|
| A61K 33/30 | (2006.01) |
| A61K 31/718 | (2006.01) |
| A61K 9/00 | (2006.01) |
| A61K 9/10 | (2006.01) |
| A61K 31/721 | (2006.01) |
| A61K 31/7016 | (2006.01) |

(52) U.S. Cl.
CPC ............ *A61K 33/30* (2013.01); *A61K 9/0014* (2013.01); *A61K 9/10* (2013.01); *A61K 31/7016* (2013.01); *A61K 31/718* (2013.01); *A61K 31/721* (2013.01)

(58) Field of Classification Search
CPC ..................................................... A61K 33/30
See application file for complete search history.

(56) References Cited

U.S. PATENT DOCUMENTS

| | | | |
|---|---|---|---|
| 3,667,472 A | 6/1972 | Halpern | |
| 3,812,252 A | 5/1974 | Silvetti | |
| 4,414,202 A | 11/1983 | Silvetti | |
| 4,600,574 A | 7/1986 | Lindner et al. | |
| 5,496,872 A | 3/1996 | Constancis et al. | |
| 6,046,178 A | 4/2000 | Silvetti, Sr. | |
| 8,252,333 B2 * | 8/2012 | Cueto-Garcia | A61L 15/28 424/425 |
| 8,440,227 B2 * | 5/2013 | Cueto-Garcia | A61L 15/28 424/425 |
| 2014/0200193 A1 | 7/2014 | Cueto Garcia | |

FOREIGN PATENT DOCUMENTS

| | | |
|---|---|---|
| EP | 2062602 A2 | 5/2009 |
| WO | 2008/026905 A2 | 3/2008 |
| WO | 2012/108753 A1 | 8/2012 |

* cited by examiner

*Primary Examiner* — Adam C Milligan
*Assistant Examiner* — Sarah Alawadi
(74) *Attorney, Agent, or Firm* — Hoffmann & Baron, LLP

(57) ABSTRACT

The invention relates to an anti-inflammatory composition comprising: 53 wt.-% maltodextrin in relation to the total weight; 10-12 wt.-% zinc oxide as a thixotropic agent; 1.8 wt.-% maltose; 0.0002 wt.-% sodium; 0.0002 wt.-% potassium; 0.0002 wt.-% calcium; 0.0002 wt.-% phosphor; and 0.0006 wt.-% magnesium. The composition has an application viscosity in the range of 12,000-33,000 cp, a pH of between 5.6 and 6.9, a TGA of 61.12 and bond strength at 24 hours of 6 MPa.

6 Claims, 7 Drawing Sheets

ANTI-INFLAMMATORY COMPOSITION FOR AIDING AND PROMOTING THE HEALING OF CHRONIC ULCERATIVE LESIONS

CROSS-REFERENCE TO RELATED APPLICATIONS

This application is the National Stage of International Application No. PCT/MX2014/000152 filed Oct. 1, 2014, which claims the benefit of Mexican Application No. MX/a/2013/011471, filed Oct. 2, 2013, the contents of which is incorporated by reference herein.

FIELD OF INVENTION

The invention relates to a composition with high anti-inflammatory and bacteriostatic capacity for external use in humans, and in particular to a composition useful to assist and promote the process of healing of chronic ulcerative lesions such as, for example, diabetic foot and varicose vein ulcers which are characterized by a challenging environment presenting a local and systemic chronic inflammation, ischemia, abnormal pH and bacterial effects, necrosis, and foreign bodies.

BACKGROUND OF THE INVENTION

Diabetic foot lesions (DF) of the lower extremities are a serious and common complication of Diabetes Mellitus Type 2 (NIDDM), and are a health problem, with important socio-economic and health impact, due to large use of material and human resources. They represent one of the most important expenditure items of the health systems of Mexico and all the world also due to increasing of NIDDM. DF according to the International Consensus on Diabetic Foot is an infection, ulceration and/or destruction of deep tissues associated with neurological alterations and varying degrees of peripheral vascular disease in lower extremities that affects patients with NIDDM. Patients with DF often require amputations of the lower extremities and in more than half of the cases, the infection is the predominant factor. The primary cause of DF (diabetic foot), is the damage that the progressive NIDDM produce on the nerves, which is known as neuropathy, that produces decrease or loss of sensitivity to pain, temperature and muscle atrophy, favoring the appearance foot deformities in the bone structures and instability. By decreasing or eliminating sensation in the foot, any wound no matter how small produced by excessive rubbing or increased exposure to heat or cold usually do not manifest itself and the patient does not recognize them properly and without pain that is a defensive mechanism of the organism, diabetics suffer injuries that present progress insidiously. In addition the loss of muscle control causes secondary atrophy in muscles and tendons that favors the appearance of deformities and changes in the distribution of the support of feet during walking and predispose certain points of the foot to develop injuries and wounds which, if not treated in time can be very serious, resulting in osteomyelitis in patients with DF, and once bone is infected, an amputation has to be done and may prove even fatal.

In DF ulcers an infection is confirmed in little more than half of ulcers (52%) while the harmful chronic inflammatory process is invariably present mainly due to the local and systemic insulin resistance.

Ischemia is very frequent in diabetics due to the damage to peripheral vessels and in fact in the EURODIALE study, ischemia was detected in more than 52% of patients suffering from DF. The foot is an area of deficient irrigation since it is very distant to the heart and added to this the damage suffered by blood vessels in NIDD, explains that blood circulation in DF is very decreased. Arterial perfusion is responsible for providing necessary nutrients for tissue regeneration in such a way that if a wound is present, healing will be impeded in NIDDM.

Additionally a decrease in arterial perfusion will not provide an adequate amount of medications prescribed to treat the infection in addition to their questionable efficacy. On the other hand and given the difficulties mentioned, local treatment of the wound is essential though unfortunately may not be effective.

In this regard, in the 2012 Guidelines for Treatment of DF, I.D.S.A. (American Association for Infectious Diseases) issued in November 2012, clearly states that "to date there is no solid evidence of the effectiveness . . . among the products used such as antiseptics, antimicrobials, etc., that are used locally in the treatment of DF . . . and considering that have effects side, toxicity, are expensive and some induce bacterial resistance, cannot be recommended for use. Dumville et al, arrived to similar conclusions in their systematic and extensive review and remarked that local and more expensive treatments had no advantage over the ones used that are less expensive. Another example is the use of the of negative pressure systems (NPWT) that may had mild advantages over the conventional treatments, but that given their price and accessibility cannot be recommended for widespread use.

Vascular ulcers of the lower limbs constitute an important public health problem due to the negative impact in socio-economic and health, for their use of large human and materials resources. Vascular ulcers defined as a lesion with skin loss produced by alterations of the circulation (venous and/or arterial) usually located in the lower third of the pelvic limbs which can develop into chronic ulcers.

According to their etiology, vascular ulcers of can be classified as venous, arterial and mixed. Venous ulcers are caused by a deficiency in microcirculation due to venous hypertension, valvular insufficiency and hypoxia that induces damage in the venous wall and constitute 90% of the all limb ulcers. Arterial ulcers are produced in most of cases by skin ischemia caused by arteriosclerosis and the mixed ones are due to an arteriovenous disorder.

Varicose venous ulcers are the result of a chronic increase in intraluminal hydrostatic pressure due to the failure of the venous valves that produces expansion and tortuosity of the veins, mainly on the pelvic limbs. This situation produces edema and ruptures with extravasation of blood in turn producing dissecting hematomas in soft tissues, all which exerts a direct compressive mechanical action on the skin causing chronic hypoxia, as well as an autolytic destructive process derived from a chronic inflammatory process that prevents healing and this originates the ulcers. These ulcers are characterized by a wide tissue destruction and repeatedly exacerbated by the presence of microorganisms that colonize or infect the wound producing a chronic inflammatory process that increases the ulcer size which can vary in dimension, from a few square centimeters up to large extensions uni or bilaterally.

Currently there is a diversity of therapeutic options for treatment of varicose venous ulcers mainly related to new types of bandages, with or without local and systemic therapeutic agents and with surgical modalities developed by Bioengineering technologies like extracellular matrix and growth factors and various materials for the treatment of the wounds including magistral mixtures of zinc oxide, vaseline, lanolin, starch and silver Sulfadiazine and their use in wounds and in open wounds and their use is widely advertised for due their composition it prevents adhesions to the fatty tissues or foreign bodies and also due to their components may stimulate the healing by granulation. Other materials such as the alginates, the collagen dressings, activated charcoal or silver, the foam polymers, hydrogel hydrocolloids, and polyurethanes that alone or combined with therapeutic schemes may favor venous circulation, keep the injured area aseptic and allow the formation of granulation and epithelization tissue, but none of all the mentioned to date has shown satisfactory consistent results as informed by the American Venous Forum (2011) and the Society of Vascular Surgery of the United States.

On the other hand, it is well known in state of the Art the therapeutic use of starch Hydrosilate film produced agent as described in U.S. Pat. Nos. 3,812,252 and 4,414,202. Hydrolysate starch has bacteriostatic and bactericidal effects.

U.S. Pat. No. 6,046,178 describes a composition for "treatment of external wounds" which includes a hydrolysate starch powder medication with an equivalent of dextrose less than 60, such as a non-hygroscopic maltodextrin, for the treatment of injured or open skin defects as in the case of burns, ulcers, and other types of skin injuries that are exposed to the environmental conditions and pollutants. In another embodiment, starch hidroxilate is mixed with the fluid proteins of the wound to form a film which finally adheres to the underlying tissues, being this film semipermeable to air and liquids.

In order to improve the process of healing of the wound, the composition of the U.S. Pat. No. 6,046,178 is applied in the form of a gel, being the maltodextrin non-hygroscopic, mixed with water and by adding other gelatinizing agents such as per example, Glycerin. In the U.S. Pat. No. 6,046,178 it is also described that water can be added to form a continuous phase emulsion, while the gelatinize is mixed in the continuous phase of such way that this becomes a dispersed phase to form a gel that has a final viscosity in the range of 29,000 to 37,000 cp. The weight percentage of the non-hygroscopic maltodextrin in the composition varies from 57 to 77% for form a continuous aqueous phase. The gel Composition presents advantages or benefits such as for example, an efficient delivery of dermatological agents that have a healing effect and a deeper application of these agents to the wound area. These benefits are provided by the viscosity of the composition, which necessarily requires the addition of Glycerin like an agent of gelatinization in order to provide a viscosity in the range of 29,000 to 37,000 cp. In U.S. Pat. No. 6,046,178 it is recognized that a greater viscosity of the gel of this range, would not disperse in an appropriate way the healing agents to the wound and a minor viscosity of the mentioned range would slip and not be adherent to the wound surface.

Additionally, in the U.S. Pat. No. 6,046,178 includes the use of a dressing for reducing the bacterial inoculum of an infected wound and inhibits the infection of a not infected wound. For this purpose the composition can be mixed with antibacterial agents for the prevention or treatment of a secondary infection. The dressing can be used in external environments for it is semipermeable and it allows the passage of gas and fluids that is to say that the wound can "breathe", and for that reason has to be changed several times daily. Additionally, a pharmaceutically acceptable metal can be added as a component of the composition to promote growth and development of healthy tissue and thus benefits the healing process. The addition of an additional component can improve the action of the film forming agent combined with the monosaccharide. The optional components generally do not amount to more of the 5% of the total weight of the composition.

U.S. Pat. No. 6,046,178 does not describe that the composition possess anti-inflammatory activity that contributes and favors the healing process of chronic ulcerative lesions such as diabetic foot and varicose venous ulcers.

U.S. Pat. No. 4,600,574 describes a tissue adhesive where a biocompatible material such as a polysaccharide is combined with a solution that contains Fibrinogen and Factor XIII. Due to the presence of fibrin this adhesive has the disadvantages that are described subsequently.

U.S. Pat. No. 5,496,872 describes a not-toxic biodegradable adhesive for surgical use. This composition contains a mixture that possesses at least two different functions that can be used in combination with polypeptides and/or biodegradable polysaccharides, synthetic or natural.

Efforts for developing synthetic polymers have been made such as, by example, cyanoacrylates as adhesives and biomedical sealers. A tissue adhesive is described in U.S. Pat. No. 3,667,472 of Halpern, which is related with the use surgical of adhesives Mono-medic of the drug Agents called alkylating agents of C2-C4 alpha-cyanoacrylate. This tissue adhesives based on cyanoacrylate are polymerized at the contact with water or blood and forms a solid layer crystallized over the tissue layer. However a disadvantage of this kind of adhesives is that is contraindicated for application in internal organs or in vascular surgery due to their toxicity and oncogenic effects that have been well demonstrated.

The well known associated toxicity with synthetic adhesives led the researchers to the development of adhesives biologically derived as materials of union. A type of adhesive or biological derived glue is an adhesive based on fibrin. The commercial tissue adhesives of fibrin are obtained of human plasma which raises the potential for health risks. The fibrin (and its derivatives) have been used in the formulation of biomedical adhesives in a limited manner and with variable results; experimentally and prospective human studies cannot be made for obvious reasons. However, the use of fibrin has various disadvantages: there is the risk of viral transmission like any other cryo-precipitate, processes of extraction blood are required, costs are high, special form of applicators and required and there a substantial risk of allergic reactions. Other disadvantage that have the fibrin-based adhesives is that the force of adhesion is relatively weak compared to the collagen-based adhesives and their cost is very elevated.

More recently, products of combination have been devised to be used as tissue adhesives and sealers. Is has been described the use of a combination of three independently prepared substances, the cryo-precipitate of human Fibrinogen Thrombin in the presence of the calcium ion, and concentrate of factor XIII, in order to obtain a glue for use in biomedical applications. However this type of products and systems of adhesives available do not avoid the health problems produced by the use of products derived of the plasma or blood. Attempts have been made to isolate an analog counterpart of the component that contains Fibrinogen (see, by example, Feldman, M. C., et, Arch Otolaryngoi-Head and Neck Surg (1988) 114:182-185;) Feldman, M. C., et, Arch Opththalmol (1987) 105:963-967; Feldman, M. C., et, M J Otolog (1988) 9:302-305; [Silberstein l. e., et to, Transfusion (1988)-28:319-321]. Nevertheless, the use of preparations of the analog Fibrinogen component also has obvious limitations.

The International application No. PCT/MX2007/000098 entitled "A new adhesive biological biodegradable, not-toxic, for use in abdominal surgery" common property of the inventor of this invention, describes a formula of a not toxic biological adhesive that protects and seals the anastomosis and suture lines in the internal body, cavities, said formula includes dextrin as a dispersion, at least an agent that increases the tack time based in a metal oxide that increases the viscosity and the resistance and the force of adhesion, and optionally an antibiotic; said formula contains 80-97% by weight of dispersion of dextrin, and the dextrin dispersion contains 45 to 75% of solid based in weight total of the formula, and wherein said formula is adequate for prevent dehiscence and strengthens temporarily the anastomosis and suture line on the internal cavities of the body, and prevents the escape of secretions and bacteria. However, the International Application does not describes nor suggests that the adhesive formulation possesses a powerful anti-inflammatory or bacteriostatic effect for external use that enhances and favors the healing process of Chronic ulcerative lesions such as diabetic foot and venous varicose ulcers.

The International Application No. PCT/MX2011/000146 entitled "Biological thixotropic adhesive for use in internal cavities of the body" common property of the inventor of this invention, describes a biological thixotropic adhesive comprising dextrin, and at least a structural component that provides thixotropy to the adhesive, and optionally at least a antibiotic, and is useful to stimulate the healing of tissue in a patient, for example, to prevent dehiscence of an anastomosis in the digestive system of a patient, to fix a prosthesis during a hernia operation in a patient and to occlude a fistula in a patient. The biological thixotropic Adhesive can be used with a patch of fatty tissue. However, the international application does not describe not suggests that the biological thixotropic adhesive possesses a powerful anti-inflammatory or bacteriostatic effect for external use that enhances and favors the process of healing in Chronic Ulcerative lesions such as diabetic foot and varicose venous ulcers.

Therefore there is a need in the state of the art technique for a composition with high anti-inflammatory and bacteriostatic properties for use external in humans. Particularly, there is a need for a composition useful in enhancing and favoring the healing process of Chronic ulcerative lesions such as for example, diabetic foot and varicose venous ulcers which are characterized by a complicated environment with local and systemic chronic inflammation, by lack of circulation, pH abnormalities, toxic bacterial products, necrosis, and foreign body effects.

There is a need for a useful composition to enhance and favor the healing process of Chronic ulcerative lesions such as for example, diabetic foot and varicose venous ulcers, that does not require of an interface, patches, dressings and similar, to help and favor the healing process of Chronic ulcers.

BRIEF DESCRIPTION OF THE INVENTION

Then, is a fundamental part of this invention, to provide a composition with high anti-inflammatory and bacteriostatic capacity at favors healing for use in Chronic ulcers in humans.

According to an additional aspect of the present invention, it is described an anti-inflammatory and bacteriostatic composition that includes mainly a non-hygroscopic maltodextrin with high stability that inhibits crystallization as an agent of dispersion and with at least an structural component that provides thixotropy and increases the tack time to the resulting composition. In base to the total weight, the anti-inflammatory and bacteriostatic composition contains 80-97% by weight of the dispersion of non-hygroscopic maltodextrin, and said dispersion of non-hygroscopic maltodextrin that contains 45-75% of solids, and has a viscosity higher than 100,000 cp in a resting state and an application viscosity on the range of 15,000 to 27,000 cp.

Considering the needs of this technique, it is an object of the present invention to provide an anti-inflammatory and bacteriostatic composition based in a non-hygroscopic maltodextrin, which is safe and effective that has the following features and properties:

I. The ingredients are non-toxic for application in human beings.

II. The composition is "THIXOTROPIC". This provides the capacity of stability like if it were solid during a long time without need of special storage conditions or cooling; when needs to be re-used it can easily be changed to semi liquid state and applied.

III. Resistant to bacterial contamination. The non-hygroscopic maltodextrins possess antibacterial properties.

IV. Biodegradable and Safe. The properties of the composition persist for several days even without a gauze or dressing that covers the lesion.

V. It has a slightly acid pH consistent, compatible with the slightly acid pH of the skin.

VI. Its viscosity in resting state is greater than 100000 cp, while the composition prepared for application, has a viscosity of 15000 to 27000 CP.

VII. Highly anti-Inflammatory Properties.

VIII. Presents a TGA of 65.12%.

BRIEF DESCRIPTION OF THE FIGURES

Several features and benefits of this invention can be demonstrated best if is displayed accompanied of some drawings, pictures and histological presentations. By example.

DETAILED DESCRIPTION OF THE INVENTION

Figure 1:
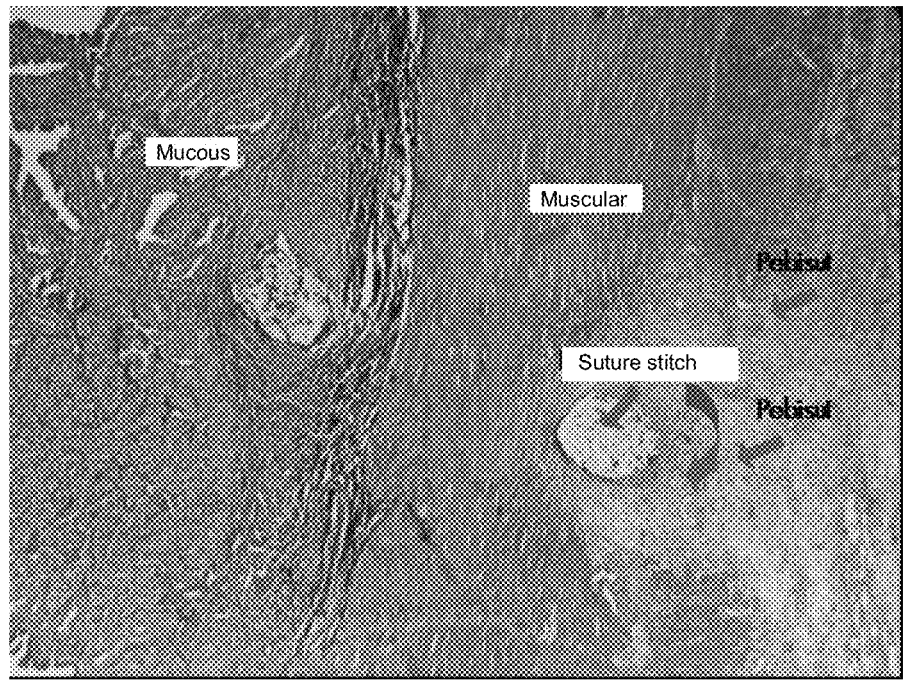
FIG. 1 is a photography—a microscopic section—, of the bowel of dog eleven days after the anti-inflammatory and bacteriostatic composition of the present invention had been applied in a suture line.

The terms "thixotropy" and "thixotropic" as used in this invention are related to the properties of some non-Newtonian and pseudoplastic fluids that show a change—time dependent—, in the viscosity; how much more is a fluid is transformed by agitation or stirring e.g.: how much shearing reduces the viscosity.

The anti-inflammatory and bacteriostatic composition of the invention is biodegradable, non-toxic, safe and has a high capacity beneficial to interrupt the chronic inflammatory process that favors the healing process.

In one aspect of the present invention, anti-inflammatory and bacteriostatic composition is mainly constituted by a natural product, easy to use and cheap, which has shown to have properties very useful in experiments carried out in several animal species is well tolerated and biodegradable all which is related to its physicochemical properties and concentration of its additional components.

According to the above, the anti-inflammatory and bacteriostatic composition of the present invention offers convenient advantages over other formulations currently available and promotes healing and a safer and shorter treatment for the patient under medical supervision since it is easily prepared and used by the patient itself and/or a relative.

Another important and very desirable characteristic is that the anti-inflammatory and bacteriostatic composition of the invention is not toxic and presents a potent anti-inflammatory and bacteriostatic, without any unwanted side effects, as is the case for example of the use of other biological compounds based in fibrin and their derivatives, that besides being expensive and complicated to use, can cause severe hypersensitivity reactions that can be very serious, even lethal. The anti-inflammatory and bacteriostatic composition of the invention is very cheap.

As such, an anti-inflammatory and bacteriostatic composition is that formulation primarily of natural origin that has the property to penetrate tissues and/or live structures and exert the enhancing of healing in all levels of an ulcer. For those said properties to be effective, there must be a intimate contact between the adherent material and the recipient tissue. Preferably, the anti-inflammatory and bacteriostatic composition of this invention should be in direct contact not only with the surface of the tissue and/or live structure, but it has to penetrate also in holes or defects of the recipient tissue.

The anti-inflammatory and bacteriostatic composition of the present invention contains non-hygroscopic maltodextrin and a structural component that provides thixotropy and improves healing. Each one of the components of the anti-inflammatory and bacteriostatic composition of the invention is present in adequate quantities to provide the before mentioned properties.

The anti-inflammatory and bacteriostatic composition of the present invention contains in addition to the non-hygroscopic maltodextrin and the structural component, maltose and also contains trace amounts of sodium, potassium, calcium, phosphorus and magnesium that gives to the final composition increased stability, since with these elements the degradation of the dextrin is avoided and also, some of these elements also directly involved in the healing process. In an embodiment of the invention, the composition contains 1.8% of maltose, 0.0002% by weight of sodium, 0.0002% by weight of potassium, 0.0002% by weight of calcium 0.0002% by weight of Phosphorus; and 0.0006% by weight of magnesium.

The term "non-hygroscopic maltodextrin" as is used in the present invention means a glucose polymer that is produced by the hydrolysis of starch and which consists of units of glucose linked together by a-1, 4 or a-1, 6 links. As is known the non-hygroscopic maltodextrins are polysaccharides (dextro-rotatory polymers) water-soluble, of different molecular weight and chemical structure, derived of the partial hydrolysis of the starch. In the biological systems is produced by the enzymatic action of the a-glucosidases on the dextrin, but industrially the conversion takes place by the addition of acids, heating or both. The non-hygroscopic maltodextrins are not susceptible to fermentation, and have antibacterial properties. The non-hygroscopic maltodextrins are also present in some vegetables during the process of germination and ripening. The non-hygroscopic maltodextrins are also classified as non-hygroscopic white maltodextrins (greater viscosity), or yellow (greater adhesiveness) and "British gums", the last one with a high grade conversion. Preferably, the non-hygroscopic maltodextrin is of high stability and it inhibits the crystallization which avoids crystals formation in time; in addition, the non-hygroscopic maltodextrin has an equivalent of dextrose (DE) of 10-11. Besides, the non-hygroscopic Maltodextrin in a preferred presentation is a white soluble powder of low sweetness, non-hygroscopic with a density of 0.5 to 0.6 g/ml.

The non-hygroscopic maltodextrins which are useful for the preparation of the anti-inflammatory and bacteriostatic compositions are those with a viscosity of 12,000-33,000 cp (for example, 15,000-32,000 cp, or 12,000-25,000 cp, or 15,000-25,000 cp, or 15,000-18,000 cp, or 30,000-32,000). In a preferred composition, a non-hygroscopic maltodextrin is used in different concentrations: (1) non-hygroscopic maltodextrin with a viscosity of 12,000-18,000 cp (or 15,000-18,000 cp), especially of 12,000-16,000 cp, where the resulting composition is a suspension that is easy to apply and has the properties mentioned previously, and other (2) a non-hygroscopic maltodextrin with a higher viscosity (e.g., 30,000-32,000 cp}, where the resulting composition is a paste. In these compositions with different viscosity, the solvent element is found (for example: water) and a structural component that provides thixotropy (for example, zinc oxide).

In these compositions the non-hygroscopic maltodextrin is used as a suspension or paste with a solvent such as water. This suspension or paste has a variable solid content: for example, 45-75%, of 55-70%, or 60-68%.

The addition of some solid to the non-hygroscopic maltodextrin for example borax, sodium hydroxide, changes certain properties of the non-hygroscopic maltodextrins such for example, viscosity, of drying time and adhesiveness.

The selection of the non-hygroscopic maltodextrin and the main component of the anti-inflammatory and bacteriostatic composition of this invention is very useful and safe in the treatment of chronic ulcer lesions such as diabetic foot, chronic varicose vein ulcers. As was mentioned previously, the selection of the non-hygroscopic maltodextrins is based also in the following properties and characteristics:

Not Toxic to Humans

After various decades of commercial use as adhesive in envelopes, with a direct daily contact and exposure with skin, the mucosa and the lips, etc. and without any secondary unwanted results known. Also an extensive literature research shows no toxicity reports. Foodstuffs made of high residue complex carbohydrates, that includes the dextrins and similar formulas are ingested daily by human beings without any toxicity and a closely related polymer is used in the production of beer. They are also used in manufacturing capsules, etc.

The use of the icodextrin is very common in hemo and peritoneal dialysis in concentrations of 4-7%. An example of the use of icodextrin is reported in U.S. Pat. No. 6,770,148 issued of Aug. 3, 2004, entitled "solution for dialysis peritoneal that contains modified icodextrins" Other groups recently have used intraperitoneal icodextrin in women with chronic pelvic inflammatory disease and infertility problems and it seems that decreases pelvic adhesions and no important side or toxic effects were observed, only some minor allergic reactions were seen.

The cyclomaltodextrins have special properties that allow them to improve the stability, solubility and biostability by the availability for oral absorption of some drugs and that is what they are used for. The cyclomaltodextrins are degraded enzymatically in the digestive system, mainly in the colon and no toxic effects are known. Due to those properties their intravenous use is currently being investigated with considerable interest.

Finally it should not be forgotten that a modified starch closely related from the biochemical point of view is frequently used as an intravenous colloid-osmotic solution in emergency situations in humans.

In our experimental work we used non-hygroscopic maltodextrin mainly. The non-hygroscopic maltodextrins, are obtained from vegetable products and have been used commercially as glues by decades. However, given the fact that other dextrins have similar properties, the inventor considers that they can be used with the same purpose of this invention. In fact, some of them are currently being used successfully in medicine in different types of applications.

Resistant to the Bacterial Colonization

The non-hygroscopic maltodextrins have potent antibacterial properties. This property is of utmost importance in the anti-inflammatory and bacteriostatic composition for the treatment of external lesions such as diabetic foot and varicose venous ulcers.

High Penetration in Microholes, Grooves or Slots

The application in porous substrates such as paper, carton, has demonstrated its high capacity to penetrate microholes, grooves or slots through the area where it is applied. For this reason in recipient tissues with such defects is important.

High Resistance to Moisture

The adhesive based in non-hygroscopic maltodextrin displays a high resistance to moisture in environments with high humidity.

It is Biodegradable

In the external environment the resistance or force of adhesion can persist for many weeks and the resulting end products are simple carbohydrates that are removed, absorbed with no harmful results. It does Not pollute the environment.

Very Cheap $2,000.00 pesos, m.n., (USD$150) a 60 Kg container.

The preferred non-hygroscopic maltodextrins for use in the formulation of the anti-inflammatory and bacteriostatic composition of the present invention (mixed with an acceptable solvent such as water) are those which exhibit a viscosity of 12-33,000 centipoise, 15,000-32,000 CP., 15,000-25,000, 15,000-18,000 cp. Although those with a viscosity of 30,000-32,000 CP., centipoise with a high content of zinc oxide also can be used. These non-hygroscopic maltodextrins (which industrially have high content of borax) and in this invention contain zinc oxide as a structural component that provides thixotropy and increases the adhesiveness to the resulting composition) require about 2 to 3 minutes more time for the application for it is a paste. The non-hygroscopic maltodextrin diluted in water (with a solids content of for example: 45-75%, or 55-70%, or 60-68%) is present in the anti-inflammatory and bacteriostatic formulation of the composition in a quantity that varies between 80% and 97% (or 90-97%, or 80-95%) or preferably of 92-96% of the total weight of the formula.

In the less viscose formulation, (12,000-16,000 cp.) the solid content of the mixture of non-hygroscopic maltodextrin and water, is of the 60-63% and has a pH of 5.6 to 6.9. This formula works well at room temperature (20-30° C.), does not require cooling or warming and is active more than 36 months stored in a dry room. The more concentrated formulas with viscosity of 30,000-33,000 CP., are a paste with all the mentioned properties previous lines but with a tack time of 4-6 minutes.

The term "non-hygroscopic" as is used in this invention means that the maltodextrin reaches a maximum moisture of 6% such as is measured using the method described in the FCC.

The structural component that gives thixotropy increases the adhesiveness used in the anti-inflammatory and bacteriostatic composition of this invention is selected from of an insoluble metal oxide powder. As is known in the technique, the use of borax can change the physical features of the non-hygroscopic maltodextrins such as for example, the viscosity, the adhesiveness, the water solubility, etc., but is also known that borax can produce granulomas in human beings. It is also known that different metal compounds (calcium, iron, titanium, zirconium, copper, zinc) can be incorporated in polymers to increase the capacity of these for tissue adherence to tissues. These metal compounds preferably be insoluble in water and have an ionisable charge in the surface of the media aqueous where are used. The addition to the polymer can be mixed with said polymer or by covering it ("coating"). Is also known that some polymers that contain metal compounds adhere actively to tissues and structures such as mesentery, fatty and connective tissue a phenomenon that we have observed with non-hygroscopic maltodextrins, that are very viscous (30,000 cp) when the anti-inflammatory and bacteriostatic composition is placed free in the peritoneal cavity without a patch or interface of a biodegradable material.

It has been found that zinc oxide powder is a structural component that gives thixotropy and increases the adhesiveness adequately for the anti-inflammatory and bacteriostatic composition based in a non-hygroscopic maltodextrins of this invention. The zinc oxide has the approval of the FDA as an pharmaceutically acceptable additive and can be ingested by humans without any collateral adverse effect and additionally zinc oxide due to its emollient, absorbent among other properties, it is uses daily in a countless applications such as wounds, decubitus ulcers, the eruption of the diaper rash in babies, etc. As was mentioned previously, zinc oxide integrated to the polymer (non-hygroscopic Maltodextrin) increases biological adhesiveness, decreases the drying period which improves the properties of the emulsion of the anti-inflammatory and bacteriostatic composition for the treatment of external lesions such as diabetic foot and varicose venous ulcers. The zinc ion finally as is very well known, is a very important factor in human metabolism and in the healing process.

The structural component that provides thixotropy is present in the anti-inflammatory and bacteriostatic composition of the present invention in a quantity suitable to modify the adhesive resistance of the adhesive to allow that the anti-inflammatory and bacteriostatic composition can stay in the external lesion. The adequate quantity of this structural component that provides thixotropy in the anti-inflammatory and bacteriostatic composition is such that is important help in the healing process. The structural component that provides thixotropy is present in the formulation of the anti-inflammatory and bacteriostatic composition in an amount that varies from up to 19% in the total weight of the formulation, most preferably between 8-12% by weight, and very preferably the structural component that gives thixotropy and increases the adhesiveness is present in a quantity of 9% to 11% in the total weight of the formulation. Also the use of zinc oxide is very cheap and the cost is similar to the cost of the non-hygroscopic maltodextrin.

In a preferred particular embodiment, the anti-inflammatory and bacteriostatic not toxic composition of this invention is a thixotropic viscous liquid with a viscosity between 17,000 to 25,000 cp, a pH slightly acid of 5.6 to 6.9, a TGA of 61.12 and presents adhesiveness at 24 hours of 6 MPa. TGA by its acronym in English (thermal gravimetric analysis) is a test commonly used in research and tests and determines the features of materials such as polymers, to determine the temperature of degradation, etc.

The determination of the TGA is done using a Thermogravimetric Analyzer brand Ta instruments, model TGA 2050. For this analysis the samples were warmed of up 100° C. (with controlled heating speed) the oven is isothermal until the sample arrives to a constant weight value.

The Adhesiveness can be measured using an Universal machine of Mechanical tests brand Instron, model 5500 R. and it was done using the test method of Joined adhesive to a time of 24 hours with a separation of jaws of 5 cm and with a separation speed between the jaws of 1 mm/min.

Due to the fact that there are extensive solid both clinical and experimental evidence that extensive bacterial invasion interferes with the healing process, the anti-inflammatory and bacteriostatic composition of this invention has shown that does not requires the inclusion of a complementary antibiotic.

Also other acceptable pharmaceutically agents can be added to the formula. For example: growth factors can be added and also for example: those substances that in small amounts injected on the wounds stimulate the growth of new blood vessels—called angiogenesis—, which is critical for the development of new tissues such as collagen, for production of keratinocytes, fibroblasts, etc. These growth factors are produced mainly in the macrophages present in the wound like other various cytokines in the initial phase of the healing process of and other like the platelet factor 1 (PDGF), a vascular stimulant (VEGF), the GF for queratinocites, (in the external wounds), etc. In this regard, recent evidence shows that some of these growth stimulants, in particular the platelet derived applied to humans is associated with the development of carcinomas for which reason the F.D.A. and the W.H.O. have issued notices of caution with its use.

Arginine is another major example of an additional and valuable factor that can be added. Arginine is an amino acid that play a very important role in cell reproduction, on wound healing, improving the immunocompetence, etc., and is used by the tissues to produce nitrous oxide, a vasodilator substance that plays a very important role in the healing of wounds.

Anti-Inflammatory Effect of the Composition

Figure 2:
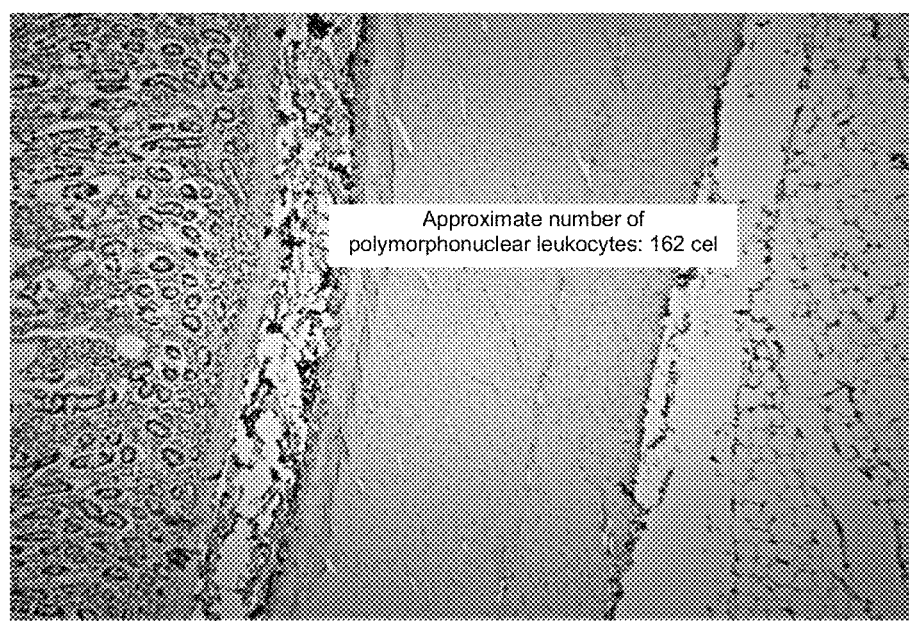
FIG. 2 is a photography—a microscopic section with Immunohistochemistry—, 10 days after the anti-inflammatory and bacteriostatic composition of the present invention had been applied in a suture line. As can be seen there is very little inflammatory reaction with scanty polymorphonuclear cells.
Figure 3:
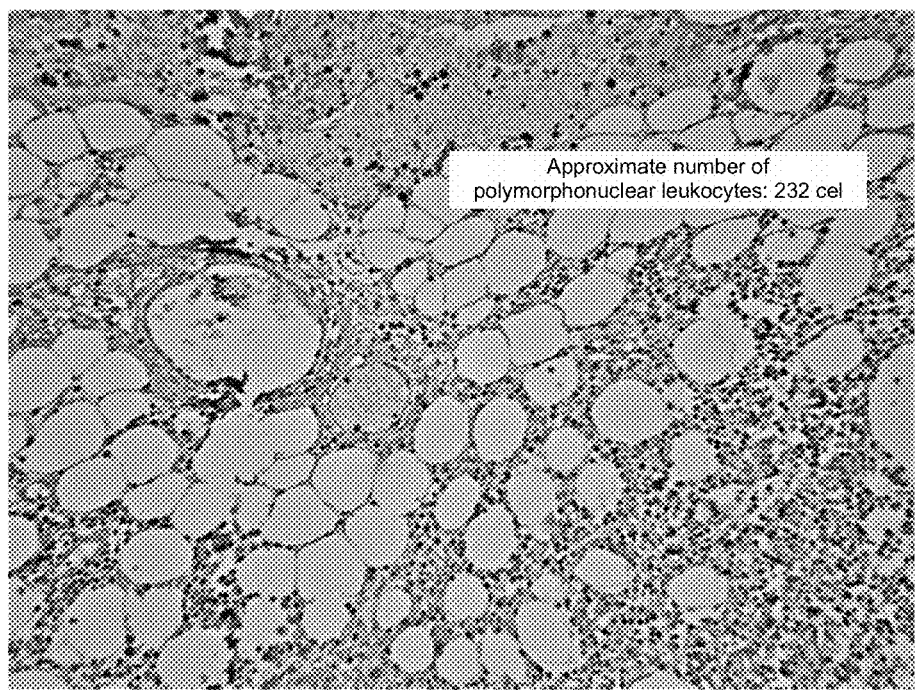
FIG. 3 is a photography—a microscopic section with immunohistochemistry—, in the same dog, 10 days after a suture line had been done and without the application of the anti-inflammatory and bacteriostatic composition of the present invention had been applied in a suture line that shows intense polymorphonuclear infiltrate, a usual inflammatory response.

The anti-inflammatory and bacteriostatic composition of the current invention has a potent local anti-inflammatory effect based on the findings of the accompanying figures. Eleven days after the application of the anti-inflammatory and bacteriostatic composition in chronic experiments in dogs with bowel suture lines, the composition has penetrated up to the mucosa and as can be seen clearly there is not inflammatory reaction (FIG. 1). In such FIG. 1 can it be seen that eleven days after the application of the anti-inflammatory and bacteriostatic composition, the composition extends in all the intestinal wall and there is not an inflammatory reaction, which means that the composition is very well tolerated by the tissues of the mammals since a foreign body reaction is not produced (right bottom area). This is noted after the comparison with a section of tissues with or without the application of the anti-inflammatory and bacteriostatic composition. In the area without the adhesive, an infiltration of inflammatory cells is noted after of the creation of a defect that was subsequently sutured most inflammatory cells being polymorphonuclear leukocytes (PMNs), as is best observed in the top left area. In FIGS. 2 and 3 (Inmunohistochemistry) a similar phenomenon can be seen: ten days after 2 suture lines were done in the bowel of the same dog at a distance of 15 cm, in the area treated with the anti-inflammatory and bacteriostatic composition the inflammatory changes are minor (132 PMNs) compared to FIG. 3 where the of PMNs count is 232, which means that the composition of this invention decreases the inflammatory cell reaction. This finding could be crucial in some clinical situations—such as an anastomosis or a suture line in the in presence of peritonitis, for it is well known that infection and continuous inflammation interfere adversely with the healing process in mammalians, and the result in clinical surgery could very well be the escape of the intestinal contents in the peritoneal cavity with their serious or even lethal consequences for the patient. There are many well controlled experimental studies that document the effect deleterious of infection on the healing process.

Figure 4:
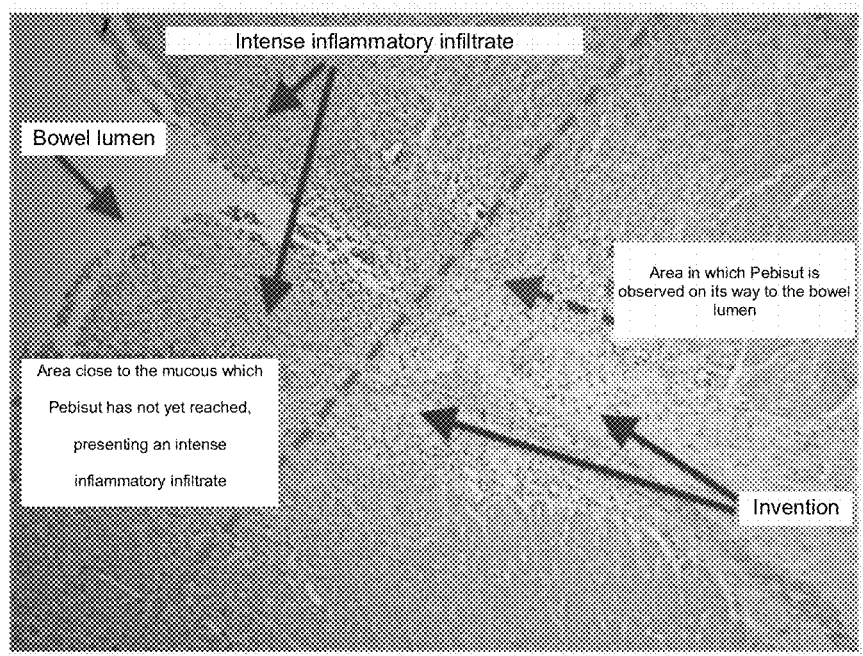
FIG. 4 is a photography—a microscopic section—, of human colon with postoperative peritonitis that and no dehiscence of the anastomosis and where the anti-inflammatory and bacteriostatic composition of the present invention had been applied in said anastomosis.

In FIG. 4 (H.E. staining) it can be seen that the anti-inflammatory and bacteriostatic composition of the present invention occupies all the intestinal wall of a human colon without any evidence of an inflammatory or a foreign body reaction or rejection Like in FIGS. 2 and 3, in the right lower area where the composition of this invention, can be seen, there is no inflammatory reaction as could be expected in a postoperative patient with peritonitis while in the top left area of the muscular layer (without the composition) an extensive inflammatory infiltrate is seen as expected in this type of septic complication. In all these figures one can see that the composition is very well tolerated by the bowel tissues of mammals including human beings.

Repeated trauma, foreign bodies, necrosis by pressure, infection, ischemia, and tissue hypoxia are some of the well known factors accepted for the production of a state chronic inflammation that is characterized by the increased number of inflammatory cells like neutrophils, macrophages and lymphocytes. Subsequently, the presences of dead tissue, bacterial products, foreign bodies are powerful chemoattractants able to keep a continuous flow of inflammatory cells. These wounds are characterized by high levels of pro-inflammatory cytokines, such as TNF and interleukins, activated collagenases, etc., and also with enzymes that degrade the matrix, including elastase. Such microenvironment of the chronic wound is characterized by an imbalance between the enzymes of degradation of the matrix and their inhibitors. Such microenvironment of the wound results in the degradation of all the protein elements found in the tissues so that the deposition of matrix cannot progress to a point where epithelization is delayed or absent. These factors setup a vicious circle capable of producing chronicity of the wounds including any effective intervention to induce healing by granulation.

Although the acute inflammatory process is very important because produces hemostasis and cleans—in a way—, the wound (bacteria, (debris, cells), also produces the accumulation of cellular and humoral factors that are very necessary for the third and fourth phases necessary for healing. On the other hand, if for some reason the second and third phases are not complete as normally occurs, which can be the case of infection, trauma, etc., then a vicious negative circle is produced that prevents healing. Currently is considered that in the normal phases, the so called M1 macrophages (pro-inflammatory) at the end of phases 1 and 2 should be transformed into macrophages M2 that are those that induce the deposition of factors that favor the conversion of collagen III to collagen 1, the angiogenesis, etc., and this progresses to phase 3 (collagen deposition), and phase 4 (remodeling, where the wound acquires tensile force because of the) formation of the matrix with collagen 1, and this completes the healing process usually called "by first intention". In reality in the chronic wounds this sequence does not occur, and the presence of granulation tissue can be found.

In the case of the infected chronic wounds, some of which have been sorely suffered by patients during months or years currently it is considered that the M1 macrophages continue activated and the result is that they continue to promote the activity of various factors humoral and cellular pro-inflammatory factors that procrastinate the vicious cycle of inflammation that directly interfere with the normal healing process.

The healing of wounds is a complex biological process that requires the well orchestrated interaction of mediators, of resident and infiltrated cells. In this context, the mesenchymal mother cells play a fundamental role for they are attracted to the wound site and they influence tissue regeneration by several mechanisms. In Chronic wounds, these processes are seriously altered. In a comparative context, the mother cells derived of adipose tissue (ASC) were treated with fluid of the acute and Chronic wounds (AWF and CWF respectively). The proliferation and migration were investigated using 3-5 (4,5-dimetiltiazol-2-il)-2,5-difeniltetrazolio (MTT) of proliferation and test of migration Transwell. The changes of gene expression were analyzed by the chain reaction of the polymerase quantificated in real time. AWF had a greater impact on the chemotaxis ASC of CWF (77.5% versus 59.8% of migrated cells). While that the proliferation was stimulated by AWF up to 136.3%, CWF had a negative effect on time proliferation (80.3%). The expression of b-FGF, a factor of endothelial vascular growth (VEGF) and of the matrix metalloproteinase-9 was strongly induced by CWF in comparison with the soft induction by AWF. These results show how much is deteriorated the ASC function in Chronic wounds. The observed effect of CWF on the ASC proliferation and migration could be an additional factor that prevents the healing process in Chronic wounds.

In addition, the prolonged presence of a high number of activated neutrophils that secrete proteases in the bed of the wound that destroys the growth factors, receptors, and the extracellular matrix that are essential for healing.

In these cases clinical and experimentally has been seen that the anti-inflammatory and bacteriostatic not toxic composition of this invention favors healing in said Chronic wounds blocking the harmful activity, late persistent activity of the M1 macrophages and the continuous recruitment and activation pro-inflammatory elements—that block the normal process—, and this favors the healing process as already mentioned. These effects have been clearly demonstrated in patients with varicose venous ulcers and diabetic foot.

The inventor of the present invention, has shown the anti-inflammatory activity of the composition, very useful in enhancing and favoring the healing process in chronic ulcers such as per example diabetic foot and varicose venous ulcers using histochemical techniques a useful tool for the histopathological diagnosis that permits the identification in situ of a cellular or tissular component through the reaction antigen-antibody which then is identified by a special marking which can be done directly or indirectly.

In a first step, the sections are incubated with the primary antigen that reacts with the specific antigen wherever this is located. In a second step, another antibody is applied (secondary antibody) against the primary antibody. The secondary antibody is united in a covalent manner (it is termed marked), and in this instance the enzyme peroxidase (an enzyme that catalyzes hydrogen peroxide, highly oxidizing). Finally, the reaction product of this enzyme is shown using as substrate 3, 3'-diaminobenzidine (DAB) which when oxidized forms an insoluble maroon product. The second step allows the amplification of the results of the reaction, since several molecules of the marked secondary antibody can be joined to each molecule of the primary antibody. As a result, the site where the Antigen is located presents more molecules of the enzyme so there is more sensitivity to the detection.

Shelftime Testing (Accelerated Stability) of the Anti-Inflammatory and Bacteriostatic Composition These tests using an appropriate methodology by experts have shown that up to 36 months the anti-inflammatory and bacteriostatic composition is still active without the need of cooling or special storage.

Bacteriological Tests in the Anti-Inflammatory and Bacteriostatic Composition

Multiple samples of the anti-inflammatory and bacteriostatic composition were submitted for microbiological tests on the surface and depth on the container. All were read like "sterile". In some instances this was made in the containers used for other purposes and not kept with sterile technique, and even after 7 days these samples remained "sterile" although the containers had been open and no antiseptic precautions were followed in these cases. The powerful bacteriostatic action of the composition was shown against *Pseudomonas* A., *Staphylococcus* A. Coagulase Positive, pathogenic *Escherichia Coli*, etc.

The concentration of solutes also plays an important role because provides the thixotropic effect and is basic for the homogeneity and stability of the anti-inflammatory and bacteriostatic composition; this is also modified by the addition of zinc oxide that acts as a structural component which also confers thixotropy to the composition, increases the viscosity and decreases the adhesiveness. Zinc ion also plays a well known and critical role in the healing process constituting part composition of the metalloenzymes. The addition of zinc oxide provides an immediate advantage in patients suffering an chronic or acute infectious process—such as septic peritonitis, residual sepsis, malnutrition, etc.—, for it is known that in these patients the serum levels of this very important trace element—ion zinc—, are very decreased.

Lesions like diabetic foot ulcers, varicose venous ulcers, decubitus ulcers and all chronic wounds are not only colonized, but very frequently infected and as generally observed, this is a polymicrobial process given the numerous courses of systemic and/or local antibiotics, and many of these germs have mutated and are resistant to the commonly used effective antibiotics. This bacterial resistance to antibiotics is a critical issue in the care of these patients and already is responsible for many grave problems: many patients will die by the germs that already are resistant to most antibiotics, and many patients will have to be treated with multiple regimes of different and very expensive new antibiotics.

The anti-inflammatory and bacteriostatic composition of this invention has a potent bacteriostatic effect against *Pseudomonas Aeruginosa* and other pathogenic bacteria and does not induce bacterial resistance for the mechanism of action is very different that the one possessed by antibiotics. In the chronic infected ulcers, the environment of the cell is very altered: decreased blood perfusion, presence of dead cells and detritus, low oxygen tension, etc., but in these lesions the most important negative factor is the existence of vicious circles that self perpetuated such as the persistence of activated M1 macrophages that continuously produce chemo-toxins and other factors that maintain the chronic inflammatory local status, the presence of very toxic free radicals, etc., all of which prevents the development of healthy granulation tissue.

EXAMPLE

The following example is given only to show in part, the claimed invention, and is not aimed to limit the scope of the invention.

Equipment Used
Mettler Toledo Scale, model SW (Max 75 kg/150 lb; Min 0.01 Kg/0.021b)
Shaker: model Eurostar Power b IKA-WERKE (50-2000 l/min)
Timing Propeller medium size.
Steel stainless Container
Potenciometer, standard
Viscometer, Brookfield
Procedure:
1. In a steel stainless container purified water was added, 33.5% of the total weight of the formulation. Then, non-hygroscopic maltodextrin was added up to 53% in of the total weight of the formula, and this was mixed with 1.8% of the total weight with maltose, sodium, potassium, calcium, phosphorus and minerals trace elements such as Magnesium.
2. Continuing with the manufacturing process, zinc oxide was added, 11.5% of the total weight of the formula increasing the speed of agitation.
3. The qualitative filling process was done up to the neck of the bottle.
4. In the final product, the appearance, color, smell and the pH and viscosity values of were determined and the following results were obtained:
Appearance: Resting: Gel, almost solid,
Prepared for use: viscous liquid.
Colour: White creamy
pH: 6.1
Viscosity: Resting: 100500 c.p., Prepared for use: 17000 c.p.
Note: the preparation of the product for use is done stirring in a circular manner using a spatula during 1 min or placing it in a container with warm water with a temperature 60°, 1 min.
Method of Application: Varicose Venous Ulcers
In the clinical Protocol, the methodological design required a program with two arms and random assignment of patients with chronic varicose venous ulcers (UVV) with the purpose to compare the response and evolution of the ulcers with the treatment with the anti-inflammatory and bacteriostatic composition of this invention against control patients treated with venous compression and cleansing of the ulcers.

Following antiseptic procedures and using venous compression in all cases, the process of healing of UVV as well as the anti-inflammatory and bacteriostatic properties of the anti-inflammatory and bacteriostatic composition of this invention was evaluated during 8 weeks and compared with the control group.

In each visit, pictures were taken and measurements of the ulcerative lesions were done to evaluate the response to the treatment.

A total of 40 patients with UVV were: 20 patients with UVV which received the treatment with the anti-inflammatory and bacteriostatic composition of the present invention and 20 were assigned to the control group.

Day 0.

Each patient was evaluated clinically for known heredo-familial antecedents, and also measurements were done to determine the extension and depth of the ulcer.

Pictures were taken with adequate equipment to help the clinical and tissular evaluation of the ulcerative lesion.

The value of the index arm-ankle was recorded.

A biopsy of the UVV was done and sent to the Immuno-biology laboratory to determine the percentage of lymphocytes T CD4, CD8, macrophages and cells CD34+ obtained by flow multiparametric Cytometry.

Subsequently, the anti-inflammatory and bacteriostatic composition was applied in all the extension of the ulcer and covered with a secondary dressing (gauze)

Application of the anti-inflammatory and bacteriostatic composition:
a) The patient removed the venous compression system to expose the ulcer.
b) The patient removed the secondary dressing (gauze) previously moistened it with clean water and dried it with an absorbing dressing.
c) the anti-inflammatory and bacteriostatic composition Is applied in all the extension of the ulcer with a tongue depressor (approximately 5 g of product in every application) following which an absorbent dressing is placed on top of the ulcer.
d) Finally, the venous compression system of 40 mm Hg is applied (gold standard treatment).
Week 2
The patient is seen in the clinic, the ulcer is exposed, the inflammatory process and tissular architecture are evaluated; the area of the lesion is measured.

Pictures with accurate equipment are taken to help the clinical evaluation of the ulcerous lesion.

The arm-ankle index is recorded.

Then, the venous compression system of 40 mmHg was removed (gold standard treatment) to expose the ulcer.

The secondary dressing (gauze) was removed previously moistened with water and cleansed, and the ulcer is dried out with an absorbent dressing. The anti-inflammatory and bacteriostatic composition is applied in all the extension of the ulcer with a tongue depressor (approximately 5 g of product) and later an absorbent dressing is placed on the ulcer.

Finally the venous system compression of 40 mmHg is applied (gold standard treatment).

Weeks 3 to 7

The patient is seen in the clinic, the ulcer is exposed, is evaluated the inflammatory process and tissular architecture; the area of the ulcer is measured.

In every session:
1. Pictures are taken with accurate equipment to help the clinical evaluation of the ulcer.
2. The arm-ankle index is recorded.
3. Subsequently, the venous compression system of 40 mmHg (gold standard treatment) is removed to expose the ulcer.
4. The secondary dressing (gauze) is removed previously moistened and cleansed with water and dried out with an absorbent dressing.
5. The anti-inflammatory and bacteriostatic composition is applied in all the extension of the ulcer with a tongue depressor (approximately 5 g of product) and then a humectant dressing is applied on the ulcer.
6. Finally the venous compression system of 40 mmHg is applied (gold standard treatment).
7.

Week 8

The patient was seen in the clinic, the ulcer was exposed, the inflammatory process and tissular architecture were evaluated; the area of the ulcer was measured.

Pictures were taken with accurate equipment to help the clinical evaluation of the ulcer.

The arm-ankle index was recorded.

A biopsy of the ulcer was done and sent to the laboratory of Immunobiology to determine the percentage of lymphocytes T CD4, CD8, macrophages and cell CD34+25 using multiparametric flow Cytometry. Then, the anti-inflammatory and bacteriostatic composition is applied in all the extension of the ulcer and is covered with an absorbent dressing (gauze) and finally, the compression venous system therapy of 40 mmHg is applied, known as the gold standard treatment.

The results of said clinical study in the treatment group are superior to the control group with faster healing (30%) and very well accepted by the patients since the composition basis of this invention, is very easy to store, prepare and apply. The more interesting, unexpected and dramatic finding was the improvement of the quality of life that the patients referred, for in three to four days after the application of the composition, the pain, burning and the secretions virtually disappeared and the patients did not have to seek and take medications, nor ointments, and were able to sleep and walk normally.

Figure 5A:
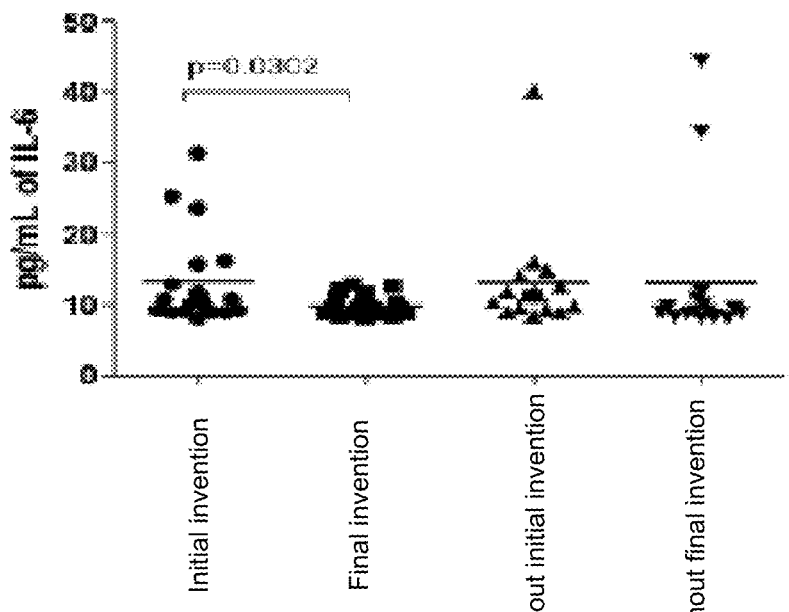
FIGS. 5A and 5B. These are graphics that show the results of molecular studies inflammatory cytokines in patients with varicose vein ulcers treated with and without the anti-inflammatory and bacteriostatic composition of the present invention.
Figure 5B:
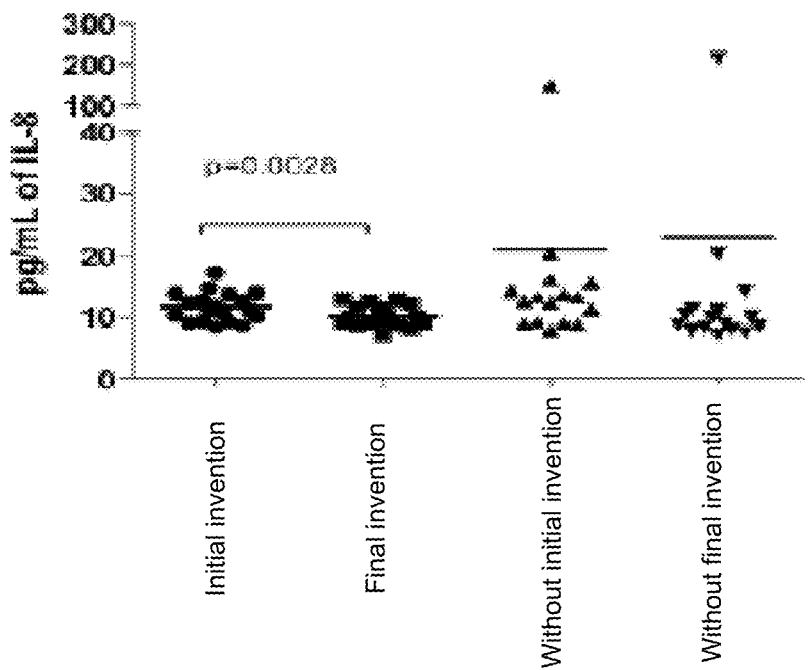
Figure 6A:
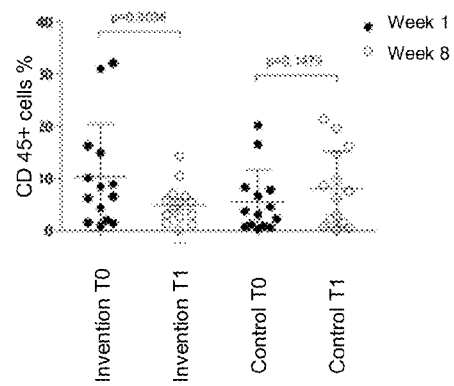
FIGS. 6A and 6D. These are graphics that represent the difference in inflammatory molecules in patients with varicose venous ulcers after 8 weeks of treatment with and without the anti-inflammatory and bacteriostatic composition of the present invention.
Figure 6B:
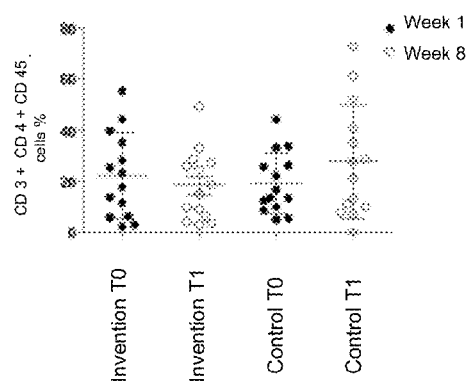
Figure 6C:
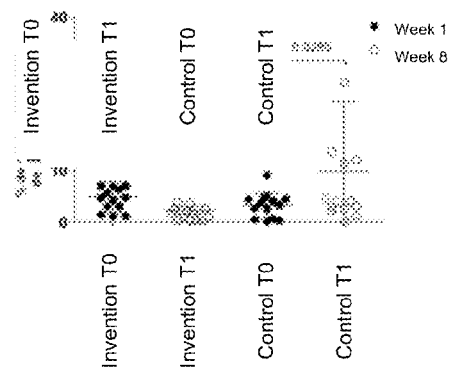
Figure 6D:
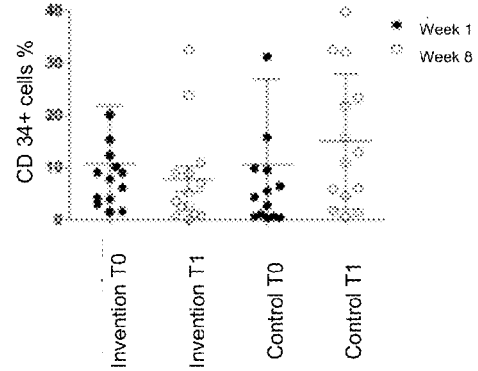

To document these findings with a scientific method, in our laboratory, molecular determinations were made of pro inflammatory cytokines IL-6, IL-8 in patients with UVV and as can be seen in the FIGS. 5A and 5B, the serum levels of systemic inflammatory cytokines decreased: IL-6 ($p=0.03$) and IL-8 ($p=0.002$) in a significant manner after of 8 weeks of treatment with the anti-inflammatory and bacteriostatic composition compared to the control group levels as is shown in the following table.

| Initial Composition | Final Composition | Without Initial | Without Final |
|---|---|---|---|
| IL-8 (pg/ml) | | | |
| 13.72 | 12.88 | 15.61 | 14.14 |
| 13.80 | 11.43 | 147.91 | 214.57 |
| 13.90 | 12.67 | 12.67 | 11.36 |
| 12.31 | 12.08 | 13.38 | 7.48 |
| 14.77 | 10.36 | 13.77 | 8.82 |
| 12.78 | 7.06 | 13.27 | 7.16 |
| 12.80 | 13.01 | 14.29 | 8.32 |
| 17.23 | 11.67 | 12.39 | 10.16 |
| | | 7.87 | 8.97 |
| 10.11 | 9.30 | 9.05 | 7.90 |
| 11.13 | 9.98 | 16.09 | 20.32 |
| 11.18 | 9.17 | | |
| 11.92 | 9.93 | 11.33 | 11.05 |
| 10.69 | 8.59 | 20.35 | 10.00 |
| 8.57 | 9.30 | | |
| 8.42 | 8.94 | | |
| 9.40 | 9.07 | | |
| 9.27 | 8.77 | 9.37 | 10.46 |
| 10.34 | 10.54 | 8.94 | 8.59 |
| 9.15 | 8.17 | 8.82 | 7.95 |
| IL-6 (pg/ml) | | | |
| 10.94 | 12.64 | 40.08 | 44.30 |
| 31.36 | 11.73 | 11.37 | 10.89 |
| 11.78 | 12.10 | 9.68 | 9.12 |
| 23.62 | 10.39 | 12.62 | 9.15 |
| 16.19 | 12.84 | 16.03 | 10.18 |
| 10.18 | 9.59 | 14.85 | 11.87 |
| 10.80 | 11.03 | 9.31 | 8.31 |
| 15.72 | 9.86 | 11.37 | 9.05 |
| | | 11.85 | 8.92 |
| 25.28 | 8.71 | 9.03 | 8.38 |
| 10.80 | 8.78 | 14.15 | 34.37 |
| 9.68 | 8.40 | | |
| 12.89 | 9.47 | 10.41 | 9.68 |
| 9.29 | 8.66 | 11.89 | 8.75 |
| 9.31 | 9.49 | | |
| 9.12 | 8.66 | | |
| 9.01 | 10.05 | | |
| 8.92 | 8.17 | 9.86 | 8.15 |
| 8.08 | 8.34 | 8;92 | 8.17 |
| 8.96 | 9.47 | 8.40 | 9.54 |

Additionally, laboratory tests were carried out to determine the frequency of inflammatory cells found in biopsies in patients with UVVC to document the molecular explanation of the faster healing with the use of the composition of the present invention: as can be seen in FIGS. 6A to 6D, the treatment with the composition showed in the biopsies of the ulcers, that exists an increase of the cell endothelial (CD 31) compared with the control group a finding that is related with the growth of granulation tissue and that the number of cytotoxic lymphocytes was greater in the control group. That Is to say, the treatment with the composition decreased the percentage of infiltrated inflammatory cells (cell CD45+) way significantly ($p=0.003$) in the patients with UVV and there was no difference on the percentage of CD45+ cells in the control group (that did). In the group of patients that did not receive composition the percentage of lymphocytes T cytotoxic was significantly greater (CD45+, CD3+ and CD89+).

| Composition T0 | Composition T1 | Control T0 | Control T1 |
|---|---|---|---|
| Biopsy (% of cell CD45+) | | | |
| 14.90 | 6.980 | 1.15 | 8.70 |
| 6.52 | 5.310 | 8.26 | 14.50 |
| 8.39 | 6.460 | 3.05 | 0.53 |
| 1.94 | 5.830 | 0.29 | 2.78 |
| 1.50 | 2.950 | 0.68 | 9.52 |
| | | 0.93 | 1.53 |
| 8.88 | 5.460 | | |
| 0.92 | 2.900 | 4.44 | 19.50 |
| | | 2.16 | 16.10 |
| 1.41 | 1.420 | | |
| 4.31 | 2.520 | 7.71 | 6.38 |
| | | 6.61 | 7.48 |
| 31.00 | 0.093 | 0.59 | 2.17 |
| 10.00 | 10.500 | | |
| 32.10 | 14.200 | | |
| 16.20 | 4.110 | 20.10 | 0.12 |
| 6.16 | 1.190 | 16.50 | 0.82 |
| | | 3.69 | 21.40 |
| Biopsies (% of cell CD31+) | | | |
| 3.76 | 7.63 | 0.40 | 6.61 |
| 10.60 | 17.76 | 10.20 | 7.25 |
| 15.90 | 13.00 | 8.34 | 1.06 |
| 7.52 | 5.66 | 6.25 | 4.96 |
| 2.91 | 3.86 | 5.21 | 16.70 |
| | | 2.77 | 4.14 |
| 9.48 | 10.59 | | |
| 1.40 | 15.60 | 19.30 | 6.16 |
| | | 0.53 | 13.60 |
| 1.89 | 2.87 | | |
| 2.57 | 4.45 | 6.84 | 3.23 |
| | | 0.31 | 9.81 |
| 25.10 | 20.27 | 0.24 | 0.25 |
| 15.60 | 18.68 | | |
| 12.30 | 21.70 | | |
| 6.84 | 7.89 | 16.00 | 48.20 |
| 4.70 | 5.43 | 11.30 | 8.48 |
| | | 2.04 | 16.20 |

Material and Methods:

Processing Blood Samples

A tube of blood with anticoagulant (EDTA) is centrifuged to 2500 rpm during 10 min to 4° C. to separate the plasma, that was stored in aliquots at −70° C. until the measurement of the inflammatory cytokines was done.

Determination of Inflammatory Cytokines and Anti-Inflammatory Cytokines in Serum Using Flow Cytometry.

For the quantification of inflammatory cytokines in serum or plasma the system Cytokine Bead Array (CBA) of BD Biosciences was used, following the manufacturer indications. In order to do it, in a tube for Cytometry a volume of the suspension with the pearls for detection of the cytokines respectively was placed with the reagent of detection (which contains fluorochrome Phycoerythrin) plus a volume of 50 microliters of serum of buffer, it was mixed and incubated during 3 hour in the dark at room temperature and after this maneuver, cleaning of the content was done and the contents of each tube was re-suspended in 200 µl of PBS. Then, the contents were processed with the Cytometry of flow (BD Accuri™ C6 Flow Cytometer) and the subsequent analysis with the software APF Array V3.

Analysis of the Cellular Percentages of the Biopsies.

The Procedure consisted in taking biopsies of 4 mm², that were placed in a 4 mL tube with the transport medium (buffered phosphate solution). After this the samples were removed from the transport medium, they were washed with a buffered of separation (PBS 1×2 mM EDTA, pH 7.4—Pharmacia—BSA to the 0.5%) to delete the blood and if needed, with the aid of a sterile syringe. Following this procedure a portion of about 2 mm² was placed in an Eppendorf previously marked with a content of 500 µl of a buffer of separation and the process continued to do the technique of mechanical disaggregation.

Mechanical Disaggregation: a tissue portion was transported to the Medicon® using clamps with a 1 ml of cushion of buffer of separation and two sectioning cycles of per minute were done in the Medimachine® (BD). With the aid of a disposable sterile syringe, the suspension was aspirated and filtered in Filcons® of 70 µm, to proceed to washing with 6 ml of buffer of separation. The suspension was centrifuged to 2000 rpm during 10 minutes to discard the supernatant; lastly the bottom was resuspended in 200 JJI-buffered phosphate followed by staining of multiparametric flow Cytometry. The percentage of total leukocytes (CD45+), cooperator T lymphocytes (CD45+, CD3+yCD4+, lymphocytes T cytotoxic (CD45+, CD3+ and CD8+, macrophages (CD34+) and endothelial cells (CD31+) with the respective antibodies, then the samples were obtained on the flow Cytometry (BD Accuri™ C6 Flow Cytometer and analyzed with the software of Flox V10)

In healthy conditions inflammatory cytokines should not be detected, the presence of detectable levels of cytokines in serum is proportional to the level of inflammation in the individual.

When mentioning detectable levels, these should be higher than:

| | |
|---|---|
| IL-8 | 3.6 pg/ml |
| IL-113 | 7.2 pg/ml |
| IL-6 | 2.5 pg/ml |
| IL-10 | 3.3 pg/ml |
| TNF, | 3.7 pg/ml |
| IL-12p70 | 1.9 pg/ml |

Figure 7:
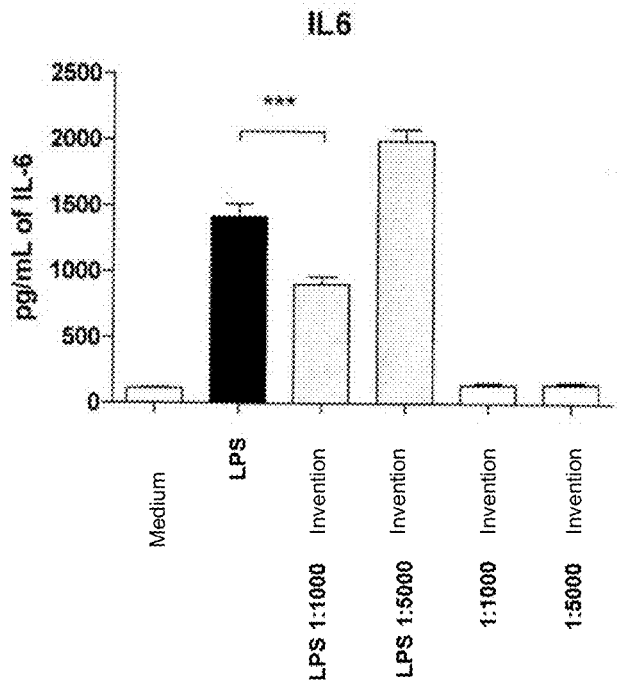
FIG. 7. This graphic shows effect of an inflammatory stimulus (LPS: a polysaccharide of the *E. Coli* endotoxin) on human mononuclear cells and the changes in IL-6 in the control group and the group treated with the anti-inflammatory and bacteriostatic composition of the present invention.

In these molecular studies to demonstrate the anti-inflammatory properties of the anti-inflammatory and bacteriostatic composition, the following results can be seen:

In an In vitro experiment and with mononuclear human cells, in FIG. 7 can be seen that with the inflammatory stimulus (polysaccharide endotoxin LPS) of control, the addition of the anti-inflammatory and bacteriostatic composition decreases the response of the IL-6 (interleukin 6 that is pro-inflammatory) using very large dilutions. If the composition is applied without dilution, the effect should be more intense.

Figure 8:
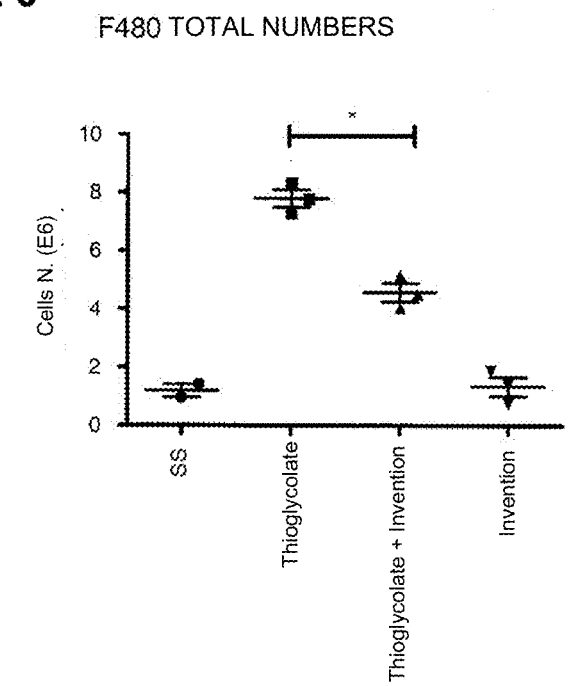
FIG. 8 is a graphic that shows the in vivo recruitment of macrophages in peritoneal cells by thioglicolate in the control group and the group treated with the anti-inflammatory and bacteriostatic composition of the present invention.
Figure 9:
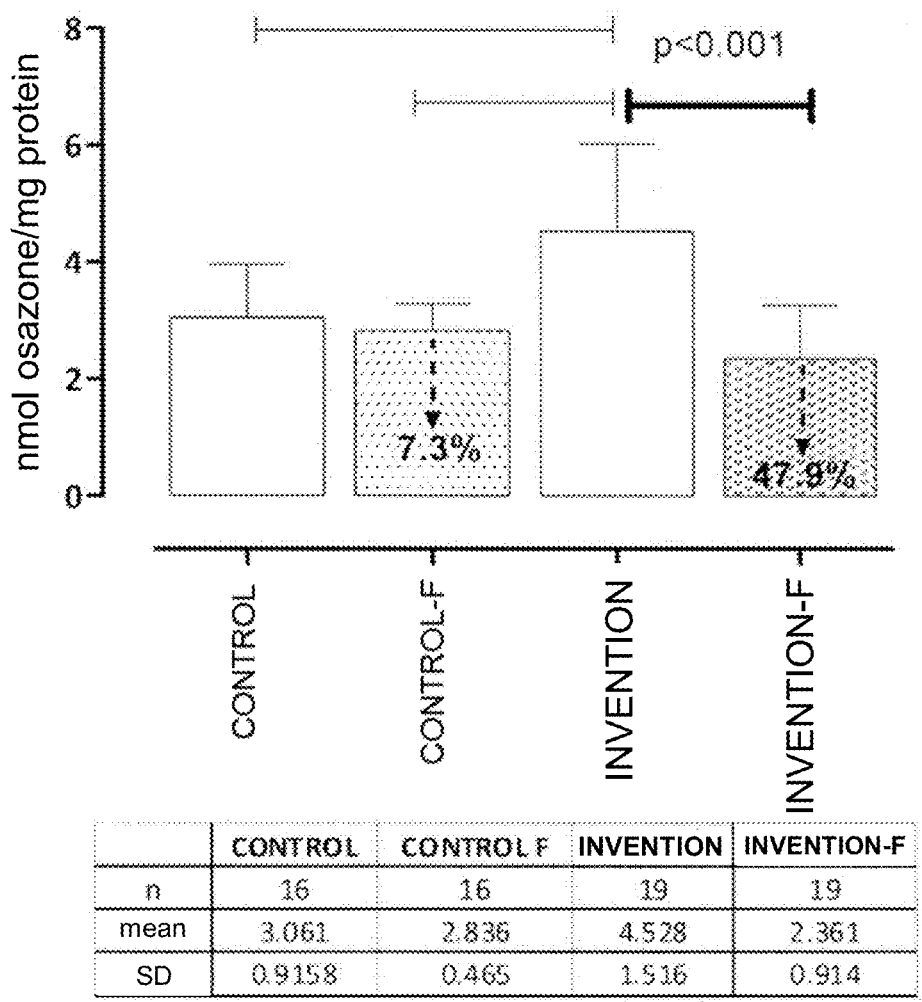
FIGS. 9 and 10 is a graphic that shows the changes in free toxic radicals (oxidative stress) in patients in both the control group and the anti-inflammatory and bacteriostatic composition of the present invention.
Figure 10:
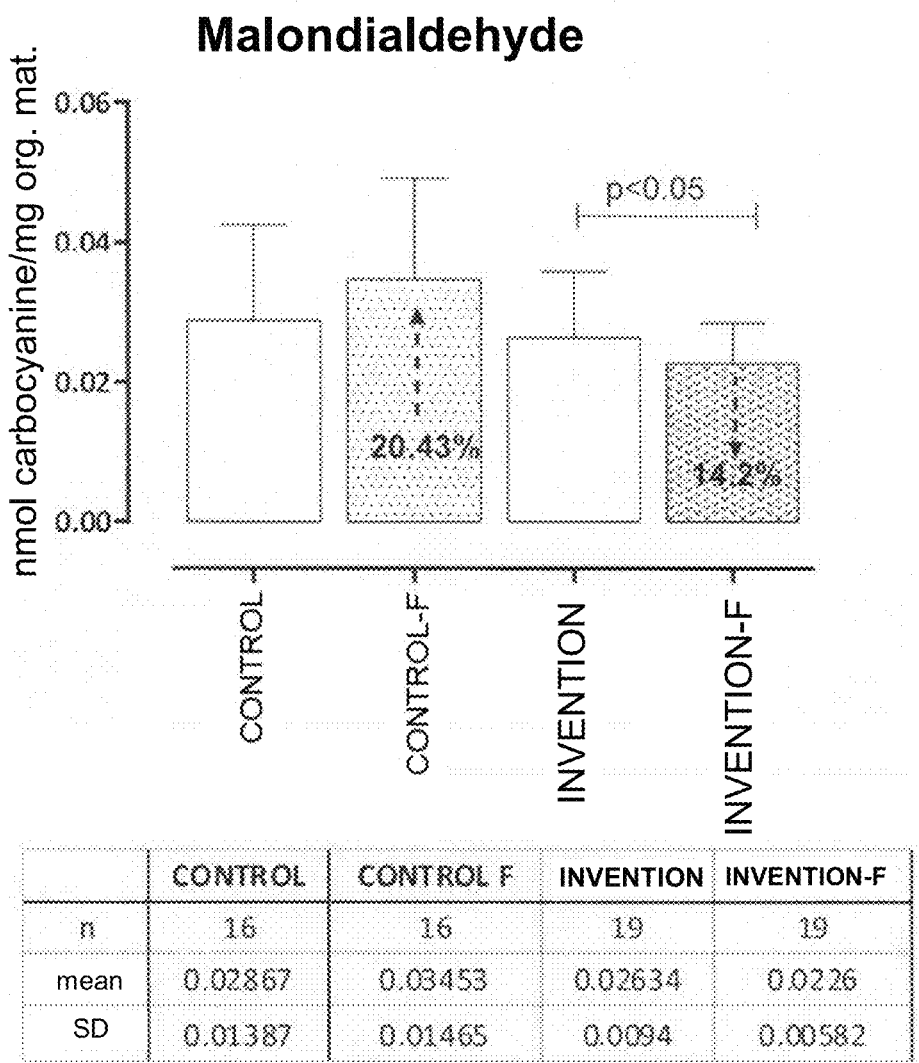

In experiments in live mice, the peritoneal cells following the inflammatory stimulus of Thioglycolate (2nd column), in FIG. 8 is noted a significant decrease of the response for recruitment of macrophages when the anti-inflammatory and bacteriostatic composition is added (3rd column). Similar results can be seen in the level of Chemokines. The dilutions of the anti-inflammatory and bacteriostatic composition are very large, and the therapeutic effect in the patient, with direct undiluted application will be much higher.

The anti-inflammatory and bacteriostatic composition of this invention offers a safe, effective and cheaper alternative to these patients with DF and UVV and other chronic non-healing lesions. Is easy to prepare and apply by the patient and/or relatives, does NOT require cooling NOR sterile instruments NOR specialized personnel.

Biomarkers of the Oxidative Stress in the Study of Patients with Varicose Venous Ulcers:

Malondialdehyde Determination (MDA)

MDA is one of the end products of lipoperoxidation. In order to quantify MDA, 301 µL of plasma are taken to whom is added MPI (1-METHYL-2-PHENYLINDOLE) [15 Mm], and HCl up to 37%. The reaction is incubated at 40° to 45° C. When the incubation is finished is centrifuged at 10,000 rpm during 5 minutes, the absorbance is determined in a Perkin Elmer UVNID model 8050-9914 at 584 nm, using Tetraetoxipropane (TEP) as standard solution (Gerard-Monnier et al, 1998).

Determination of Carbonylation of Proteins

One of the biomarkers more used to assess damage to proteins is quantification of carbonyls group (Dalle-Donne et al, 2003).

100 µl of plasma are mixed with 1 ml of 2, 4-Dinitrophenylhydrazine (DNPH) 10 mM in HCl 2.5 M.

The samples are incubated to room temperature avoiding the incidence of light (they were stirred every 15 minutes during 60 minutes) and precipitated with trichloroacetic acid (TCA) at 20%. They were centrifuged during 10 minutes at 3500 rpm for collection of the precipitated protein. The pill was washed again with 1 ml of TCA at 10%. Finally the precipitate is washed with 3 ml of a mixed ethyl ethanol-acetate of (1:1 v/v), to delete the surplus DNPH. It was centrifuged again and the end precipitate was dissolved in 1 ml of Guanidine hydrochloride 6 M in potassium phosphate 20 mM, and incubated during 10 minutes at 37° C. Finally it was analyzed spectrophotometrically at a wave length of 370 nm (Dalle-Donne, 2003).

The coefficient of molar extinction of Dinitrophenylhydrazine is of $e=22,000/m-1$ $cm-1=22,000/10^6$ nmol/ml, which is used to calculate the concentration of carbonyls, expressed in nmol of dinitrofenilhidrazonas/mg of protein quantified by the method of Lowry.

Determinations Biochemical of Stress Oxidative Markers in Plasma:

Definition of Lipohidroperoxides:

The lipidic lipohidroperoxides are molecules relatively stable, but some iron reduced compounds catalyze their breakdown to produce alcoxyl radicals; also reaction of the radical peroxyl can occur with reduced iron. Alcoxyl and peroxyl radicals stimulate the chain of reactions of lipid peroxidation, extracting hydrogen atoms of other non saturated fatty acids.

For the quantification of lipohidroperoxides in plasma an iodometric method is used (E I Saadani et ael., 1989) which consists of adding to 20 uL of plasma, a commercial reactive of Merck, cat. name 141061 CHOLPAD (used to measure cholesterol esters) and potassium iodide of 1 M. This mixture was incubated during 30 minutes at room temperature protecting it from light. The concentration of lipohidroperoxides is determined spectrophotometrically in a Perkin Elmer UVNID model 8050-9914 to 360 nm. Terbutyl hydroperoxide is use as standard.

Currently there are not sufficient studies that determine normal values in this type of population and due to the diversity used in experimental methodology to determine these biomarkers, is not possible to extrapolate these data to our population, and for that reason the normal values used are those of the control group. These were: Lipohidroperoxides: 0.047±0.004 nmol in 13/mg, organic matter Malondialdehyde: 0.03±0.0057 nmol carbocianina/mg, organic matter Carbonylation of proteins: 3.00±0.22 nmol of dinitrofenilhidrazonas/mg protein.

These markers were obtained from peripheral blood and NOT from the ulcers.

The Carbonyl and MDA mainly are the ones that signal the that ulcer is producing an inflammatory phenomenon that not only affects the ulcer and the same leg, but that are also present in all the body. As can be seen in the graphic the effect of PEBISUT is awesome because decreases all of them in a significant manner, although is applied locally in a leg.

Each Figure has the table legend at the bottom.

In general terms the characteristic initial inflammatory process of the UVV necessary to favor the cleansing of tissues and the concentration of factors required for healing. However, this process is not only is complex but is fragile and is susceptible to be interrupted or fail, when chronic inflammation is present and that interrupts the healing process.

In the inflammatory phase, bacteria are engulfed and removed along with detritus, and is free many factors that produce the migration and division of the cells that take part on the proliferative phase are liberated. The activated leukocytes secrete inflammatory mediators among them: PAF, leukotrienes and cytokines and a cytotoxic download of oxygen reactive species (ERO) that represent a mediator of tissue damage that lead to the cellular death and necrosis in many inflammatory processes. The presence of ERO can damage macromolecules like proteins, DNA, carbohydrates, and lipids. Such is the case of the results obtained proteins and MDA) in which it can be postulated that there is damage to lipids and proteins. This damage can affect membranes (lipids) structural elements (proteins) or the core nucleus of the cell (DNA) that would in time produce damage to the tissues.

The effect the composition of this invention in reference to the decrease of the biomarkers of the Oxidat Stress in the study of UVV, means that probably improves the imbalance between the production of free toxic radical and their disposal in the tissues. Said systemic consistent elevations are associated with the development or worsening of several grave conditions in different apparatus and systems.

Method of Treatment for Diabetic Foot Lesions

This will be done in 20 patients with diabetic foot lesions to whom the anti-inflammatory and bacteriostatic composition will be applied and 20 patients (control group) that will be treated with silver nanocrystals dressings used routinely on the clinic.

Week 1

1. Each patient will be evaluated clinically for known background inherited familial pathologies and also the extension and depth of the lesion will be measured. The NIDDM treatment on the corresponding clinic will be verified 2. In case of suspicion, if necessary—suspected of osteomyelitis—x-rays of the foot patient will be taken (AP and oblique of the affected limb), which can be requested again if this is determined by the medical personnel).

3. Pictures with adequate equipment will be taken to help the clinical evaluation of the lesion.

4. Following the standard measures of asepsis and antisepsis and in case that is indicated, purulent and/or necrotic will be removed and drained.

5. The lesion will be washed with clean water and dried out.

6. Using aseptic and antisepsis a biopsy will be taken in the central part of the lesion and will be sent to the Immunobiology laboratory for determination of the percentage of/inflammatory (CD45+ cells), the percentage of monocytes/macrophages and the percentage of endothelial cells (CD31+) by multiparametric flow Cytometry. A 6 ml blood sample will be drawn to determine the concentration in serum of inflammatory cytokines: IL-6 and TNF and of remodelling tissue mediators: TGFβ- and VEG.

7. Cultures from the wound will be taken for microbes and will be sent to the laboratory of bacteriology for identifying the germs and their susceptibility to antibiotics. This will be done the first week of the study and subsequently according to the needs of the study.

8. Then, the anti-inflammatory and bacteriostatic composition will be applied in all the extension of the lesion and will be covered with a humectant dressing.

In the case of clinical data of infection oral antibiotics will be started based on the clinic guidelines of treatment and a culture by biopsy with antibiogram will be done.

Note: the treatment with the anti-inflammatory and bacteriostatic composition requires application 2 times daily motive by which the nurses and physicians must instruct to patient the adequate manner to apply the anti-inflammatory and bacteriostatic composition at home.

Application of the anti-inflammatory and bacteriostatic composition:

A. The patient must remove the gauzes, bandages or dressings to expose the lesion.
B. Once the dressing is removed the lesion is washed with clean water using a gauze and then dried out with a gauze.
C. Should be washed with water the site of the lesion and dry with an absorbent gauze.
D. The patient will then apply the anti-inflammatory and bacteriostatic composition in all extension of the lesion with a tongue depressor (approximately 5 g of product in each application), let it dry for 3 to 4 minutes for the anti-inflammatory and bacteriostatic composition penetrates and adheres and then cover it with a humectant gauze.

Week 2

1. The patient will be seen in the clinic, the dressings will be removed and the lesion exposed, and will be evaluated clinically and measurements will be made and recorded.
2. Pictures with accurate equipment will be taken to help the clinical evaluation of the lesion.
3. Under measures of asepsis and antisepsis and in cases where is indicated, purulent and/or necrotic tissues will be removed and drained
4. Using clean water the lesion will be washed and let it dry it.
5. Subsequently, the anti-inflammatory and bacteriostatic composition will be applied in all the extension of the lesion and will be covered with a humectant secondary dressing (gauze).

Week 3 to 11

The patient will be seen in the clinic, dressings will be removed and the lesion exposed to be evaluated clinically and measurements will be done and recorded.

In every session:
1. Pictures with accurate equipment will be taken to help the clinical evaluation and placing a marker at the side.
2. Subsequently, the dressings will be removed to expose the lesion.
3. The secondary dressing (gauze) will be removed using a wet gauze and the lesion will be washed with clean water and later it must dried with an absorbent gauze.
4. Should be washed with water the site of the lesion and dry it.
5. The anti-inflammatory and bacteriostatic composition will be applied in all the extension of the lesion with a tongue depressor (approximately 5 g of product), let it dry 3 to 4 minutes for the anti-inflammatory and bacteriostatic composition to penetrate and adhere later place a humectant gauze on the lesion.

Week 12

The patient is seen in the clinic, the dressings removed and the lesion exposed. The lesion will be evaluated clinically and measurements will be made and recorded.

1. If necessary—suspicion of osteomyelitis—x-rays of the foot side of the lesion of the patient (AP & oblique) will be taken and can be requested again if so is determined by the doctors staff).
2. Pictures with accurate equipment will be taken to help the clinical evaluation of the lesion.
3. Following measures of asepsis and antisepsis and in case of necrotic tissues and/or purulent drainage, the lesion will be debrided and drained.
4. The lesion will be washed with abundant clean water and dry it.
5. Following measures of asepsis and antisepsis a biopsy of the central part of the lesion will be taken and will be sent to the Immunobiology laboratory for determination of the percentage of inflammatory infiltrate (CD45+ cell), the percentage of monocytes/macrophages and the percentage of endothelial cells (CD31+) by multiparametric Cytometry flow. A 6 ml blood sample will be taken for determination in serum of the concentration of inflammatory cytokines: IL-6 and TNF and remodelling tissular mediators: TGF-13 and VEG.
6. Subsequently, the anti-inflammatory and bacteriostatic composition will be applied in all the extension of the lesion and covered with humectant secondary dressing (gauze).

In the external application and depending on the size of the lesion, the amounts used with the anti-inflammatory and bacteriostatic composition vary between 4 to 6 g every time two times to the day during 8 weeks and in an average case, a simple humectant gauze is applied in the lesion; in where said composition contains 80-97% by weight of the dispersion of non-hygroscopic maltodextrin in base to the weight total of the formulation, and that such dispersion of non-hygroscopic maltodextrin contains 45-75% of solids, and also said composition contains 1.8% of total weight of maltose and wherein the anti-inflammatory and bacteriostatic composition has a viscosity greater than 100,000 cp in resting state of and an application viscosity in the range of 15,000 to 27,000 cp, a pH of 5.6 to 6.9, a TGA of 61.12 and presents an adhesiveness at 24 hour of 6 MPa.

The invention claimed is:

1. An anti-inflammatory and bacteriostatic composition comprising 53% by weight of non-hygroscopic maltodextrin, from 8 to 12% by weight of zinc oxide as thixotropy agent, 1.8% by weight of maltose, 0.0002% by weight of sodium, 0.0002% by weight of potassium, 0.0002% by weight of calcium, 0.0002% by weight of phosphorus, and 0.0006% by weight of magnesium, and the remainder water, wherein the anti-inflammatory and bacteriostatic composition has a viscosity greater than 100,000 cp and a pH from 5.6 to 6.9 for use in the treatment of chronic ulcerated lesions of diabetic foot and varicose ulcers.

2. The anti-inflammatory and bacteriostatic composition according to claim 1, wherein the composition is a dispersion containing non-hygroscopic maltodextrin mixed with water.

3. The anti-inflammatory and bacteriostatic composition according to claim 1, wherein the composition has a content of solids of 60 to 68% of the total weight of the composition.

4. The anti-inflammatory and bacteriostatic composition according to claim 1, wherein the non-hygroscopic maltodextrin has a dextrose equivalent (DE) of 10-11.

5. The anti-inflammatory and bacteriostatic composition according to claim 1, wherein the composition has a pH of 6.1.

6. The anti-inflammatory and bacteriostatic composition according to claim 1, wherein the non-hygroscopic maltodextrin is a white soluble powder of low sweetness non-hygroscopic with a density of 0.5 to 0.6 g/ml.

* * * * *